(12) United States Patent
Holman et al.

(10) Patent No.: US 12,171,676 B2
(45) Date of Patent: Dec. 24, 2024

(54) MAGNETICALLY DEPLOYABLE URINARY STENT

(71) Applicant: GYRUS ACMI, INC., Southborough, MA (US)

(72) Inventors: Thomas J. Holman, Princeton, MN (US); Nikhil M. Murdeshwar, Maple Grove, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 355 days.

(21) Appl. No.: 17/188,579

(22) Filed: Mar. 1, 2021

(65) Prior Publication Data

US 2021/0267779 A1 Sep. 2, 2021

Related U.S. Application Data

(60) Provisional application No. 62/984,059, filed on Mar. 2, 2020.

(51) Int. Cl.
*A61F 2/91* (2013.01)
*A61F 2/95* (2013.01)

(52) U.S. Cl.
CPC .............. *A61F 2/91* (2013.01); *A61F 2/9517* (2020.05); *A61F 2210/009* (2013.01)

(58) Field of Classification Search
CPC ...... A61F 2/90; A61F 2/86; A61F 2/91; A61F 2210/009
See application file for complete search history.

(56) References Cited

U.S. PATENT DOCUMENTS

| 5,851,218 | A | * | 12/1998 | Lev | ............................ | A61N 2/02 |
| | | | | | | 606/198 |
| 2006/0217754 | A1 | | 9/2006 | Boehm et al. | | |
| 2009/0287293 | A1 | * | 11/2009 | Mailhot, Jr. | ............. | A61F 2/91 |
| | | | | | | 623/1.15 |
| 2014/0336752 | A1 | | 11/2014 | Ginn et al. | | |
| 2015/0290000 | A1 | * | 10/2015 | Hansen | ..................... | A61F 2/04 |
| | | | | | | 606/198 |

(Continued)

FOREIGN PATENT DOCUMENTS

| EP | 2944293 B1 | 4/2017 |
| WO | WO-8805317 A1 | 7/1988 |
| WO | WO-2021178312 A1 | 9/2021 |

OTHER PUBLICATIONS

"International Application Serial No. PCT/US2021/020289, International Search Report mailed Aug. 10, 2021", 7 pgs.

(Continued)

*Primary Examiner* — Sarah A Long
*Assistant Examiner* — Raihan R Khandker
(74) *Attorney, Agent, or Firm* — Schwegman Lundberg & Woessner, P.A.

(57) ABSTRACT

A stent, shunt, or plug, for at least partial insertion into a patient, can include a deformable elongated tubular body including a proximal portion and a distal portion and defining a longitudinal lumen of the tubular body therebetween. The deformable elongated body can be capable of an expanded state and a collapsed state. The tubular body can include a sheath and a plurality of magnetizable or magnetic elements for providing magnetic repulsion, after being magnetically actuated, to maintain the tubular body to maintain the expanded state.

8 Claims, 10 Drawing Sheets

(56) References Cited

U.S. PATENT DOCUMENTS

2016/0242893 A1* 8/2016 Joshi .................... A61F 2/01
2020/0029951 A1* 1/2020 Bessler .............. A61B 17/0401

OTHER PUBLICATIONS

"International Application Serial No. PCT/US2021/020289, Written Opinion mailed Aug. 10, 2021", 7 pgs.
"International Application Serial No. PCT/US2021/020289, International Preliminary Report on Patentability mailed Sep. 15, 2022", 9 pgs.

* cited by examiner

MAGNETICALLY DEPLOYABLE URINARY STENT

CROSS-REFERENCE TO RELATED APPLICATION

This application claims the benefit of priority to U.S. Provisional Patent Application Ser. No. 62/984,059 filed on Mar. 2, 2020, the content of which is incorporated herein by reference.

BACKGROUND

A human kidney filters waste products from the blood and excretes these substances and excess water in the form of urine. A calyx section of the kidney serves as a beginning of a urine collecting system. A kidney typically has 6-10 calyces. Stones in the kidney can form within the calyx. A kidney stone includes a microscopic organized aggregation of salts. Procedures to treat kidney stones can include, lithotripsy and ureteroscopy.

Ureteroscopy can be used to diagnose the presence of kidney stones or to provide access for other devices such as a lithotripter, a grasper, or a stone basket. Small stones can be treated with only a stent (no lithotripsy), such as by dilating the ureter. However, if the stone is large, continues to cause problems, or the urinary system appears infected, a urologist may use an endoscope to place a small tube in the ureter. This small tube allows urine to pass, which can alleviate pain, and dilates the ureter, allowing small stones to pass. Treatment of kidney stones with ureteroscopic lithotripsy or laser fibers can create stone fragments and stone dust or "sand" as debris.

A urinary stent can be used following a lithotripsy procedure, such as to help pass fluid, stones, or sand debris, such as resulting from kidney stone fragmentation. A urinary stent can be placed in the ureter to aid the flow of urine from the kidneys to the bladder. Urinary stents can provide a temporary treatment to physically relieve an obstruction in the ureter. A urinary stent can include an elongated hollow plastic tube, such as can run the length of the ureter, and can catch or hold to the kidney and bladder on either end, such as with "pigtail" type curls. The urinary stent can be of a lateral diameter that may cause pain or discomfort when inserted into the ureter, and thereafter, depending on how long the stent is left inside the patient. When the urinary stent is later removed, whether by a thread or an office procedure, pain can again occur.

Additionally, a urinary stent may not necessarily maintain patency over the lifetime of the stent, which patency provides passage of fluids through the stent. For example, stent tubing can collapse, kink, or dent. An open, expanded, and unobstructed stent, maintaining patency with the passageway in which it resides, can allow for proper function of that stent to help pass fluids through the stent.

SUMMARY/OVERVIEW

The present disclosure describes, among other things, an in-vivo magnetically configurable compliant stent, shunt, or plug, such as can be inserted into a pathway in a collapsed state. An internal permanent magnet or other electromagnetic applicator can be used to provide an in-vivo magnetic field. The magnetic field can be used to help expand the stent, shunt, or plug, such as circumferentially or longitudinally within the pathway. One or more magnetized elements of the stent, shunt, or plug can maintain the expanded configuration during in vivo deployment. Such expansion can help provide an open lumen or to conform to a physiological wall or passage or other structure. The stent, shunt, or plug can be made of a thin, compliant material such as a polymer, such as with embedded magnetizable material that, when subject to a magnetic field, can be magnetized such as to create or maintain an expanded stent, shunt, or plug configuration.

Some stents have minimal luminal area for the passage of debris and fluid through that stent. This is due, in part, to the desire for the stent to be inserted into a patient passageway, limiting the lateral size or diameter of the stent for insertion purposes. The diameter of the stent can limit the amount of available luminal area.

Some stents, shunts, and plugs can also be rigid and uncomfortable for patients when inserted, such as due in part to their more rigid, less compliant material, which can allow for insertion and placement in the body.

Discussed herein is a highly compliant magnetically deployable stent, shunt, or plug. The magnetically deployable device can include a deformable tubular body. The deformable tubular body can include a sheath defining a luminal area and magnetizable elements to allow for magnetic configuration of the device such as while the device is located within a passageway. The device can have a collapsed morphology state, such as for insertion into the passageway. The device can have an expanded morphology state, such as for providing patency within the passageway. The device can be actuated to transition between the collapsed state and the expanded state, such as using a magnetic or electromagnetic applicator. The applicator can be used to establish or alter the magnetic field in and around the device, which can induce attraction or repulsion between the magnetic features, such as for compelling the sheath to collapse or expand. The device can be selectively magnetized, such as when or where desired, such as for ease of delivery, removal, or creating, increasing, or maximizing luminal area or to counteract effects due to strictures.

Such magnetizable, deformable stents, shunts, or plugs, can help allow for ease of insertion and removal, or to help allow for maintaining patency to provide passage of fluids therethrough, or to help establish a tamponade for sealing or plugging a passageway to inhibit passage of fluids therethrough.

For example, a stent for at least partial insertion into a patient can include a deformable elongated tubular body. The deformable elongated tubular body can include a proximal portion and a distal portion, and can (optionally) define a longitudinal lumen of the tubular body therebetween. The deformable elongated body can be capable of actuation to transition between an expanded state and a collapsed state. The tubular body can include a sheath and a plurality of magnetizable or magnetic elements such as for providing magnetic repulsion, after being magnetically actuated, such as to help the tubular body to maintain the expanded state. In some cases, the expanded state can maintain patency and fluid flow in the passageway. In some cases, the expanded state can allow for plugging of the passageway to prevent fluid or debris flow through the same.

In an example, a stent for at least partial insertion into a patient can include a deformable elongated tubular body. The tubular body can include a proximal portion and a distal portion and define a longitudinal lumen of the tubular body therebetween. A magnetic applicator can be used to actuate the deformable elongated body to transition between an expanded state and a collapsed state. The tubular body can include a sheath and a plurality of magnetizable or magnetic elements such as for providing magnetic repulsion, after being magnetically actuated, such as to help the tubular body to maintain the expanded state.

In an example, a method of actuating a stent can include inserting, to a desired location, a collapsed elongated tubular body including a proximal portion and a distal portion and defining a collapsible longitudinal lumen of the tubular body therebetween. The tubular body can include a plurality of magnetizable or magnetic elements, which can be actuated such as to provide magnetic repulsion such as to encourage the tubular body to maintain a more expanded state.

In an example, a method of maintaining patency in a body lumen of a patient can include inserting, to a desired location, a collapsed elongated tubular body including a proximal portion and a distal portion and defining a collapsible longitudinal lumen of the tubular body therebetween. The tubular body can include a plurality of magnetizable or magnetic elements, which can be actuated to provide magnetic repulsion such as to help maintain the tubular body in an expanded state conforming to walls of the body lumen, thereby maintaining patency in the body lumen.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

A stent, shunt, or plug, such as a urinary stent, can be compliant, such as to allow for ease of insertion into a passageway in a collapsed state, for later expansion. The discussed stents, shunts, or plugs can include a deformable tubular body having a collapsible sheath and one or more magnetizable elements. The stent, shunt, or plug can be inserted into a passageway in a collapsed state, for ease of insertion. In vivo, the stent, shunt, or plug can be expanded such as by applying or manipulating a magnetic field with a magnetic or electromagnetic applicator that interacts with the one or more magnetizable elements such as to expand the stent, shunt, or plug within the passageway. The device can help provide an open lumen or to conform to a physiological wall or passage or other structure.

Figure 1A:
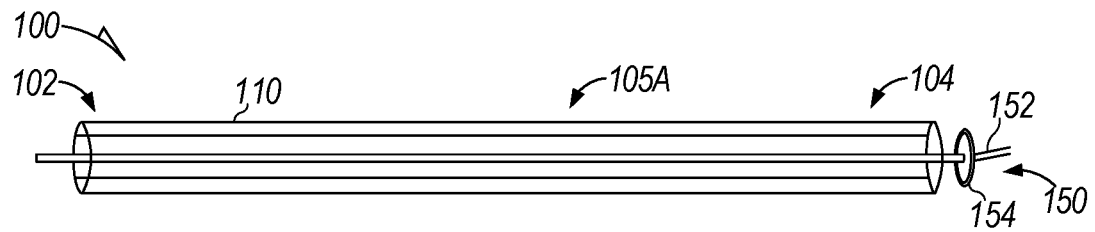
FIG. 1A illustrates a schematic diagram of a device, such as a stent, shunt, or plug, with radial expansion.
Figure 1B:
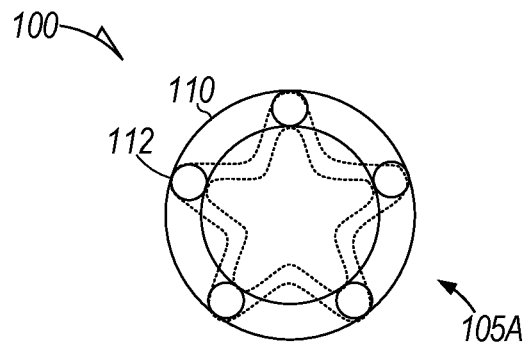
FIG. 1B illustrates a schematic cross-sectional view of the stent of FIG. 1A in an open position.
Figure 1C:
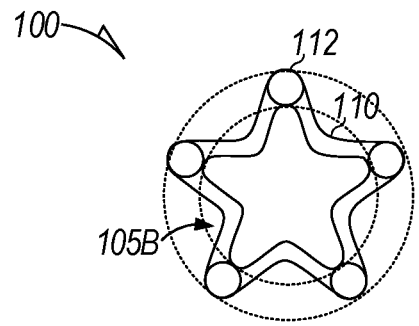
FIG. 1C illustrates a schematic cross-sectional view of the stent of FIG. 1A in a closed position.
Figure 1D:
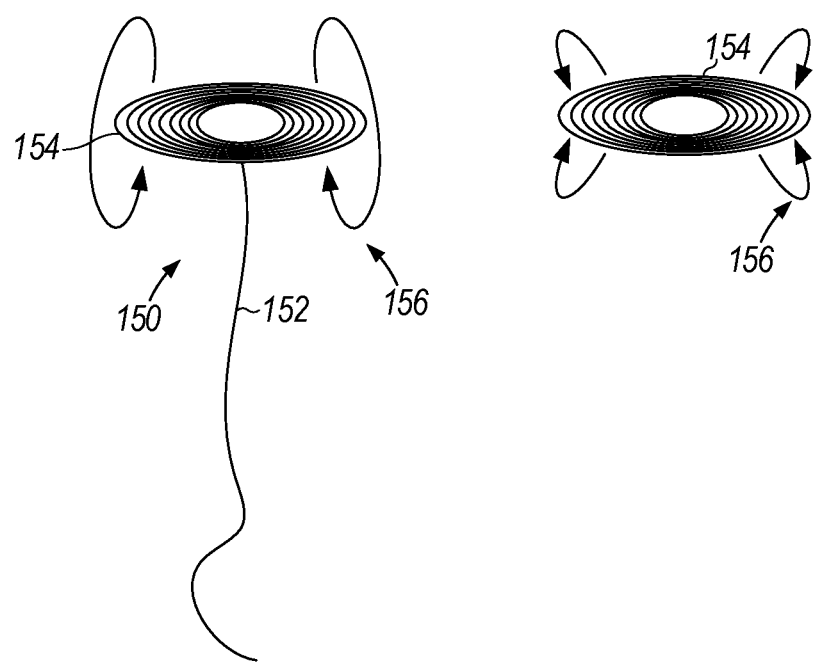
FIG. 1D illustrates an applicator for a device with radial expansion.
Figure 1E:
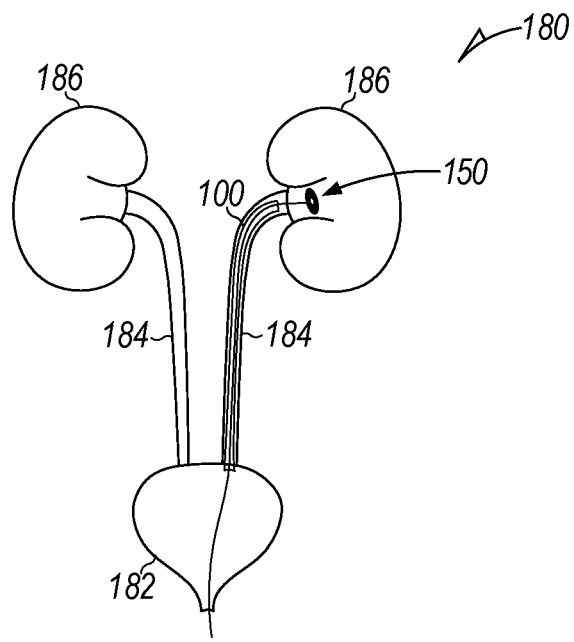
FIGS. 1E-1F illustrate placement of a device with radial expansion in the ureter.
Figure 1F:
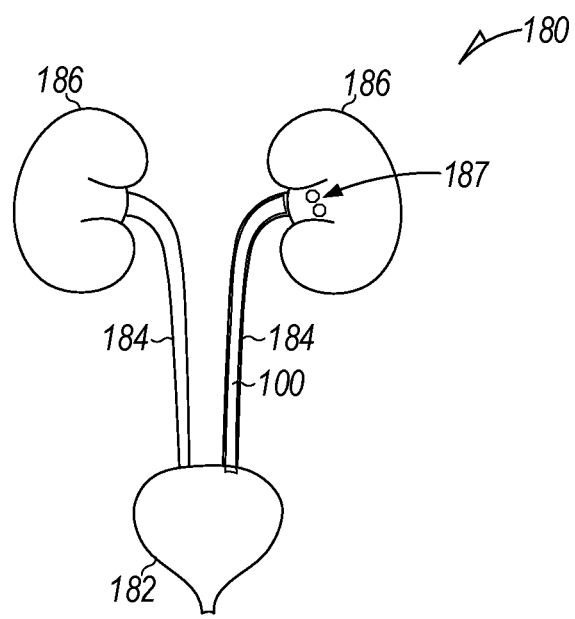
Figure 1G:
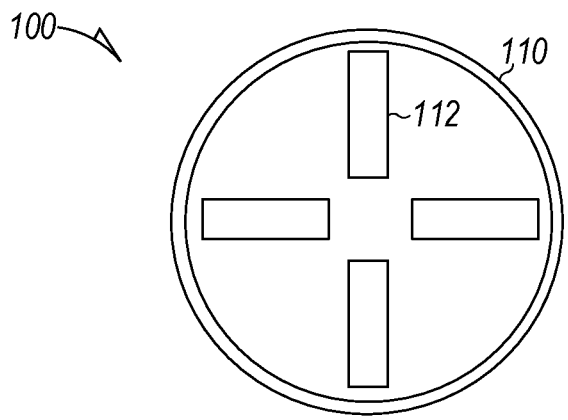
FIGS. 1G-1I illustrate a device with filamentous wires.
Figure 1H:
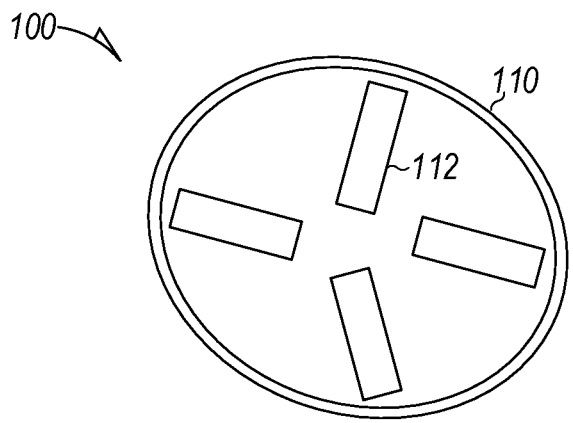
Figure 1I:
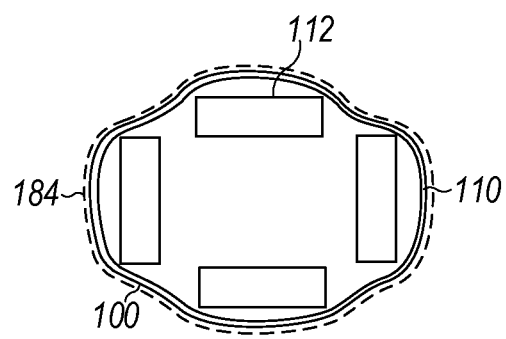

FIGS. 1A-1I illustrate a schematic diagrams of a device 100, such as a stent or shunt or plug, capable of radial expansion. Device 100 can be removed after a period of time, left in a patient permanently, or may biodegrade within the patient. FIGS. 1B-1C illustrates a schematic cross-sectional view of the device 100 in open and closed positions. FIG. 1D illustrates an applicator 150 for the device 100. FIGS. 1E-1F illustrate placement of the device 100 capable of radial expansion in the ureter. FIGS. 1G-1I illustrate a device 100 with filamentous wires. FIGS. 1A-1I will be discussed together.

In some cases, the device 100 can be a stent, shunt, or plug for insertion into a patient passageway. The device 100 can be a stent for maintaining patency of a patient passageway such as to allow fluid and debris flow therethrough. The device 100 can be a shunt such as for an alternative path for the passage of the blood or other body fluid. The device 100 can be a plug such as for preventing flow of fluid through the passageway.

The device 100 can be sized, shaped, or arranged for partial insertion of the tubular body 105 into a passageway of the patient. The device 100 can include a proximal portion 102, a distal portion 104, a deformable elongated tubular body 105 with a sheath 110 and a plurality of magnetizable or magnetizable or magnetic elements 112. The device 100 can be placed or actuated with the applicator 150, which can include a guide wire 152 and a magnet 154.

In device 100, the tubular body 105 can extend from the proximal portion 104 to the distal portion 102. The proximal portion 104 can be for holding, securing, or manipulation of the device 100, directly or indirectly, such as by a surgeon or doctor using the device 100 for a medical procedure. The proximal portion 104 can optionally be connected to one or more grips, handles, or guidewires, as desired for the operator.

The distal portion 102 can be configured for at least partial insertion into a body lumen of a patient. For example, where the device 100 is a urinary stent, the body lumen can be a ureter passageway, such as after a removal of kidney stones, to maintain patency in the body lumen for passage of fluid or debris unrestricted from the kidney to the bladder.

The deformable elongated tubular body 105 can be capable of an expanded state 105a and a collapsed state 105b, such as shown in FIGS. 1B and 1C. In the expanded state, the tubular body 105 can have a diameter of about 0.5 mm to about 2.0 mm. In the expanded state, the tubular body can be located against an inner wall of a body passageway such as to help maintain patency of the passageway. For example, if the device 100 is a urinary stent, it can press against the inner wall of the ureter once deployed and in the expanded state. In some cases, the expanded state can distend the body passageway, if desired. The expanded state of the tubular body 105 can have a diameter that is comparatively larger than some other stents, such as to allow passage of fluid and debris therethrough.

In the collapsed state, the tubular body 105 can have a diameter of about 0.5 mm to about 2.0 mm. In the collapsed state, the tubular body 105 can be collapsed in on itself such as to make a shape with a diameter or other lateral dimension that can be smaller than those of conventional or other stents. This can allow for easy insertion by the operator into a passageway of a patient.

The sheath 110 can include a compliant material extending between the distal portion 104 and the proximal portion 104, forming the tubular shape and defining a luminal space, such as a longitudinal lumen in the tubular body 105. The sheath 110 can be made of a thin-walled polymer, such as polyethylene, silicone, or polyether block amide. The sheath 110 can have a thickness of about 0.002" to about 0.01". In some cases, the sheath 110 can include more than one layer of material. The sheath 110 can have about a Shore D durometer of about 0.005' to about 0.04". The sheath 110 can define a luminal spaced with a diameter of about 1 mm to about 20 mm when in an expanded state and less than about 2 mm when in a collapsed state. In an example, the ratio of diameters in the expanded and collapsed state can be about 10:1. In an example, the ratio of diameters in the expanded and collapsed state can be about 25:1. In an example, the ratio of diameters in the expanded and collapsed state can be between about 10:1 and about 25:1. When in a collapsed state, the device 100 can be inserted into a patient passageway by itself or in a delivery sheath or shell such as can help it maintain its collapsed search such as during insertion.

The magnetizable or magnetic elements 112 can be embedded in, attached to, or coupled with the sheath 110. Magnetic materials can include those that exhibit a response to a change in magnetic field, and can include materials that are aligned to a particular magnetic field. Similarly, magnetizable materials can include those that are capable of being magnetized, and can include materials that are not yet magnetized but could be when exposed to a magnetic field.

The magnetizable or magnetic elements 112 can be at least two magnetic or magnetizable elements in the tubular body 105. In some cases, elements 112 can be a group of wires that are woven or braided around a core. In some cases, elements 112 can be actuated selectively. When magnetized, or exposed to a magnetic field, the magnetizable or magnetic elements 112 can repel each other, forcing the sheath 110 to open to the more expanded state. This can allow for the sheath 110 to be magnetically disposed outward to the body passageway wall. The magnetic repulsion between the magnetizable or magnetic elements 112 can allow for the device 100 to be suspended within a passageway and/or facilitate retention of the device 100 in a passageway, such as without need for other securing mechanisms, such as "pigtails," catches, clips, or other components. Instead, the magnetic force can, in some cases, be used to hold the device in place within a passageway and maintain patency.

In some cases, two, three, four, five, or more magnetizable or magnetic elements 112 can be used in the device 100. At least two magnetizable or magnetic elements 112 can be used to allow for magnetic repulsion between those elements when actuated. By manipulating the number and placement of wires, the diameter or other lateral dimension of the device 100 in the expanded state can be controlled.

In device 100, the magnetic elements can be magnetizable or magnetic elements that are elongate members, and can run along the length of the tubular body 105 from the distal portion 104 to the proximal portion 102. The placement of the magnetizable or magnetic elements 112 around the circumference or periphery of the sheath 110 can allow for radial expansion when the magnetizable or magnetic elements 112 are actuated to repel each other. Also, as discussed in more detail with reference to FIGS. 2A-2B and 3, the magnetizable or magnetic elements 112 can be situated so that they induce axial expansion, such as instead of, or in addition to radial expansion. In some cases, the magnetic repulsion can be sufficient to cause conformal contact between the device 100 and wall that define the body lumen into which it is placed. In this case, the expanded state can have a circular cross-section, or have a non-uniform cross-section depending on the body lumen shape.

The magnetizable or magnetic elements 112 can include wires, pieces of magnetic material, braided or interwoven strands, or other magnetic dipole inducing material. The magnetizable or magnetic elements 112 can be made of a variety of materials, such as magnetizable metallic or composite materials, or one or more combinations thereof. In some cases, the magnetizable or magnetic elements 112 can include magnetic dipole elements affixed to the sheath 110.

The magnetizable or magnetic elements 112 can run along the length of the tubular body 105 in a longitudinal direction for some or all of the length of the tubular body 105, can run along the tubular body 105 in a radial direction, can spiral around the tubular body 105, can be applied in segments along the tubular body 105, or one or more combinations thereof. The magnetizable or magnetic elements 112 can additionally be of varying types, materials, and thicknesses, so as to induce various different magnetic fields, magnetic field reactions, and magnetic repulsions, depending on how the magnetizable or magnetic elements 112 are actuated. Various patterns of magnetic elements are shown and described in more detail with regards to FIGS. 2A-2B, and FIGS. 3-6 below.

FIG. 1D depicts an example of the magnetic applicator 150. The magnetic applicator 150 can include the guide wire 152 and the magnet 154, and can be affected by a magnetic field 156. The magnetic applicator 150 can be detachable from the device 100, fully, or partially integrated with the device 100.

The magnetic applicator can include a monolithic piece, or multiple pieces, such as the guidewire 152 and the magnet 154 such as shown in FIG. 1D. The magnetic applicator 150 can include a ring such as configured to fit in or around the longitudinal lumen of the tubular body 105, such as the magnet 154. In this case, the magnet 154 can be shaped to fit inside or outside the tubular body 105, and fitted to the collapsed or expanded state of the tubular body 105.

The guidewire 152 can be attached to the magnet 154 such as to allow for manipulation of the placement of the magnet 154 in or near the device 100. This can allow for the magnet 154 to add to or change a magnetic field interacting with the magnetizable or magnetic elements 112, such as when the magnet is moved. For example, the magnetic applicator 150 can be drawn through the longitudinal lumen of the tubular body 105 to actuate the magnetizable or magnetic elements 112 to help provide magnetic repulsion to encourage the tubular body 105 to maintain a more expanded state. This can be done by the operator using the guidewire 152 to move the magnet 154.

In some cases, the magnetic applicator 150 can be drawn through the longitudinal lumen of the tubular body 105 to actuate the magnetizable or magnetic elements 112 such as to reduce magnetic repulsion to encourage the tubular body 105 to form a less expanded state. This can be done by the operator using the guidewire 152 to move the magnet 154.

In an example, the magnetic applicator 150 can be inserted into the passageway of the patient together or concurrently with the device 100. The magnetic applicator 150 can then be drawn out of the patient passageway through the device 100 to magnetize the magnetizable or magnetic elements 112 and move the tubular body 105 from a collapsed state to an expanded state.

In this case, when the operator deems it time to remove the device 100 from the patient passageway, the magnetic applicator 150 can be used to collapse the device 100 for easy removal. In some cases, the magnetic applicator 150 can remain attached to the device 100. In some cases, the magnetic applicator 150 can be removed from the device 100 during or after insertion of the device 100 into a patient passageway. The magnetic applicator 150 can be re-useable or disposable.

In some cases, the magnetic applicator 150 can be used to alter the placement or expansion of the device 100. In this case, if the operator deems that the device 100 should be adjusted, such as by a patient indicating pain or discomfort, a magnetic applicator 150 can be inserted back into the patient passageway in or near the device 100. The magnetic applicator 150 can be used to collapse part or all of the device 100, allowing the operator to re-position the device. The device 100 can then be re-expanded as desired with the magnetic applicator 150, once re-positioning has been completed.

In an example, the magnetic applicator 150 can be inserted into the passageway of the patient separately from the device 100. In this case, the operator can insert the device 100 and subsequently insert the magnetic applicator 150, drawing it up through the device to magnetize the magnetizable or magnetic elements 112 and moving the device from a collapsed state to an expanded state. In some cases, the magnetic applicator can be left in the patient and removed later when the operator is ready to remove the device 100 from the patient passageway.

The magnetic applicator 150 can allow for operator manipulation of the device 100, during insertion of the device 100, to revise or re-position the placement of the device 100, during removal of the device 100, or combination thereof.

FIG. 1E shows an application of the device 100 in a ureter 184. The urinary system 180 into which the device 100 can be applied can include a bladder 182, ureters 184, and kidneys 186. In FIG. 1E, the device 100 can be a urinary stent.

An example can include placement of the device 100 as a urinary stent for insertion into the ureter following a lithotripsy procedure. A lithotripsy procedure can include a procedure that uses shock waves or other energy to break up stones in the kidney 186 and parts of the ureter 184. After the procedure, the tiny pieces of stones can pass out of the body from the kidney, through the ureter, carried in urine. If the ureter is blocked, passage of the kidney stone fragments and urine cannot occur, and hydronephrosis, or swelling of the kidney with urine, can occur.

In this case, the device 100 can be a urinary stent for maintaining patency of the ureter and allowing passage of urine carrying kidney stone fragments for a period of time after the procedure. A urinary stent can be used to prevent hydronephrosis by allowing this passage of fluid and debris. After a lithotripsy procedure, urinary stents can be applied for three to sixth months before replacement or removal.

As shown in FIG. 1E, the device 100 urinary stent can be made of a sheath 110 of a compliant polymer material, such as polyethylene terephthalate, that can shrink to a collapsed state of within a 0.1 mil diameter. The magnetic elements 112 can include wires integrated into the sheath, made of a magnetizable material. In some cases, that magnetic elements 112 do not necessarily contiguously extend along the entire length of the device 100. In some cases, the magnetic elements 112 can be hollow. In some cases, the magnetic elements 112 can be solid.

During deployment into the ureter, the magnetizable wires 112 can be actuated with an external magnetic field, such that the sheath 110 is in a collapsed state for easy delivery into the ureter. Upon insertion into the ureter and placement, the external magnetic field can be removed, such as with a magnetic applicator 150, so that the magnetizable wires 112 repel each other and the urinary stent moves to an expanded state held in place by magnetic repulsion, allowing patency in the ureter. This is shown in FIG. 1F, where the device 100 conforms to the ureter to allow patency and passage of one or more stones 187.

FIGS. 1G-1I depict filamentous magnetizable elements 112. In some cases, the wires 112 can be filamentous, or planar ribbon-like structures with rectangular cross sections. Narrow regions of the wires 112 can face each other in the arrangement shown in FIGS. 1G-1I. During expansion of the device 100, the magnetizable elements 112 can be twisted or torqued, causing a reorientation of the device 100 such that the walls of the device 100 conform to the available space in the body lumen.

Figure 2A:
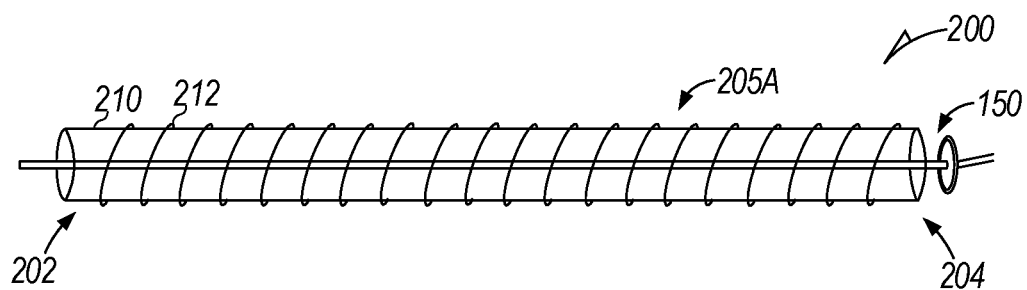
FIG. 2A illustrates a schematic diagram of a device with axial expansion in an open position.
Figure 2B:
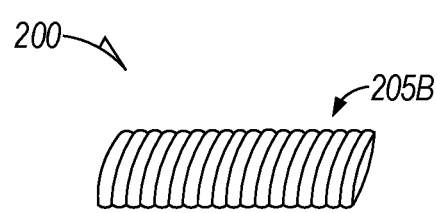
FIG. 2B illustrates a schematic diagram of a device with axial expansion in a closed position.

FIGS. 2A-2B illustrates a schematic diagram of a device 200 with axial expansion in open and closed positions. The device 200 can include a proximal portion 202, a distal portion 204, a tubular body 205, sheath 210, and magnetizable or magnetic elements 1212. The tubular body can be in an expanded state 205a and a collapsed state 205b. Device 200 is similar to and contains similar components to device 100, except where otherwise noted.

In device 200, the magnetizable or magnetic elements 212 can extend laterally along at least a portion of the tubular body 205. The magnetizable or magnetic elements 212 can spiral around the circumference of the tubular body 205, such as affixed to or embedded in the sheath 210. The magnetizable or magnetic elements 212 can extend fully or partially along one or more segments of the tubular body 205.

When the magnetizable or magnetic elements 212 are affected by a magnetic field such that the tubular body 205 collapses, the device 200 collapses in a longitudinal direction due to the placement of the magnetizable or magnetic elements 212. In this way, the collapsed state of the device 200 has a smaller lateral length than the expanded state of the same. However, the diameter of the device 200 can be unaffected by the transition to a collapsed state.

In an example, the device 200 can be used as a plug in a body passageway. For example, the operator can insert the device 200 in a collapsed state into a body passageway. Upon application of a magnetic field, the magnetizable or magnetic elements 212 can expand the device 200 along the lateral length of the pathway, maintaining the passageway width while blocking flow of fluid or debris therethrough. In this case, the ends of the device 200 can be plugged or closed to prevent fluid flow.

In an example, the device 200 can be used as a stent or shunt for a body passageway. In this case, the device 200 can be inserted in a collapsed state into a body passageway. When actuated with a magnetic field, the magnetizable or magnetic elements 212 can expand the device 200 along the lateral length of the pathway up against the wall of that pathway, allowing fluid flow through a lumen of the device 200 when expanded.

Figure 3A:
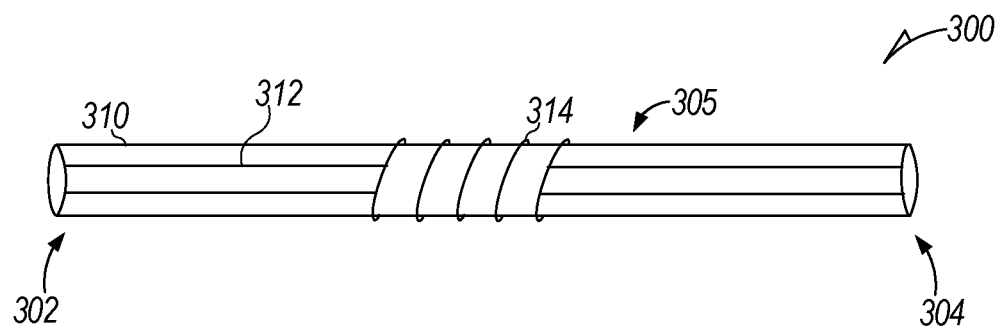
FIGS. 3A and 3B illustrate a schematic diagram of a device with radial and axial expansion in an open state.
Figure 3B:
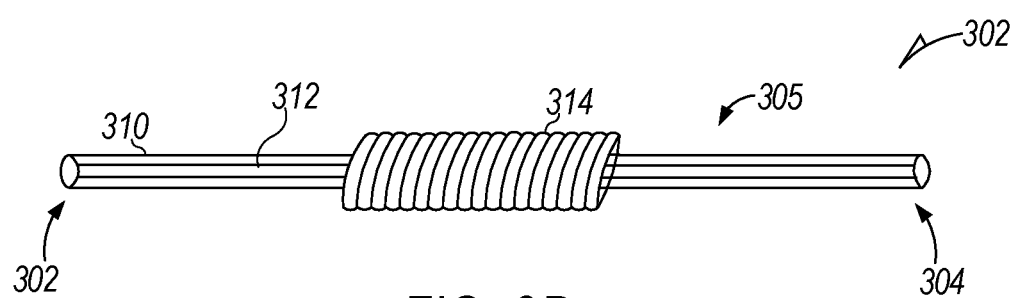

FIG. 3 illustrates a schematic diagram of a device 300 with radial and axial expansion in an open state. The device 300 can include a proximal portion 302, a distal portion 304, a tubular body 305, a sheath 310, and magnetizable or magnetic elements 312, 314. The tubular body can be in an expanded state and a collapsed state. Device 300 is similar to and contains similar components to device 100, except where otherwise noted.

Device 300 can incorporate magnetizable or magnetic elements 312, 314 in both a radial and an axial fashion, for differing portions of the device 300. In device 300, the tubular body can collapse along a central portion in a lateral manner, but can collapse in a radial manner closer the proximal 302 and distal 304 ends of the device. The device 300 can be, for example, structurally similar to a bellows, and expand or contract similar to tissue in the body.

Device 300 can be used, for example, for a particular passageway in the body that may have non-uniform diameters or other lateral dimensions, or for a passageway that intersects another passageway. The operator can manipulate the device 300 so that it expands in a radial or lateral manner to a full diameter or other lateral dimension at the proximal and distal ends 302, 304, of the device, so that the tubular body 305 fits snuggly against a wall of the passageway. The central portion hosting the magnetizable or magnetic elements 314 that are axial in fashion does not necessarily need to expand to the same diameter as the magnetizable or magnetic elements 312. In this way, the magnetizable elements can be tailored to specifically expand and collapse various portions of the device 300.

Figure 4:
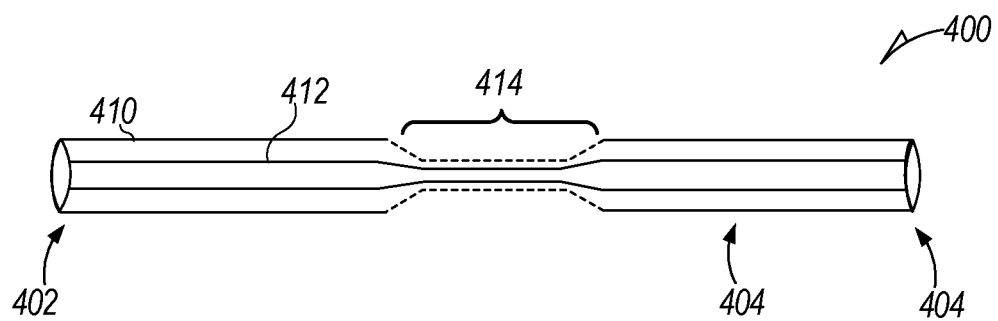
FIG. 4 illustrates a schematic diagram of a device with varying densities of magnetized wires.

FIG. 4 illustrates a schematic diagram of a device with varying densities of magnetized wires. The device 400 can include a proximal portion 402, a distal portion 404, a tubular body 405, a sheath 410, magnetizable or magnetic elements 412, and a narrowed portion 414. The tubular body can be in an expanded state and a collapsed state. Device 400 is similar to and contains similar components to device 100, except where otherwise noted.

In device 400, the tubular body 405 can contain the narrowed portion 414. In FIG. 4, this narrowed portion 414 resides between the proximal portion 402 and the distal portion 404. In some cases, the narrowed portion can be located at other areas of the tubular body 405, or multiple narrowed portions can be spaced throughout the tubular body 405. If one or more narrowed portions 414 are present in the device 400, they can be of substantially the same diameter when expanded, or of varying diameters. In some cases, a single narrowed portion 414 can be of a gradually increasing or decreasing diameter so as to create a gradient with larger diameter portions, such as proximal portion 402 and distal portion 404.

The narrowed portion 414 can be designed such that, even in an expanded state where the magnetizable or magnetic elements are repelling each other and expanding the sheath 410, the narrowed portion 414 has a smaller diameter than the proximal portion 402 and the distal portion 404. In some cases, the narrowed portion 414 can collapse and expand when the magnetic field is changed, similar to the proximal portion 402 and distal portion 402.

In some cases, the narrowed portion 414 can maintain its shape and size whether or not a magnetic field is applied. In this case, the narrowed portion may not have magnetizable or magnetic elements.

If the narrowed portion 402 contains magnetizable or magnetic elements, such as elements 412, they can be the same, similar, or different material from magnetizable or magnetic elements in the proximal portion 402 or the distal portion 404. In some cases, the magnetizable or magnetic elements in the narrowed portion can be of varying thickness, shape, or design, compared to the magnetizable or magnetic elements 412 in the other portions of the device 400.

The device 400 with one or more narrowed portions 414 can be used as a stent, shunt, or plug, in a passageway that, for example, crosses another passageway. The operator may desire to maintain patency in the first pathway, and perhaps encourage fluid flow, without inhibiting the fluid flow in the second pathway that crosses the first. In this case, the narrowed portion can be aligned where the first and second pathways meet. This can allow for fluid flow around the device 400 in the second fluid pathway.

Figure 5:
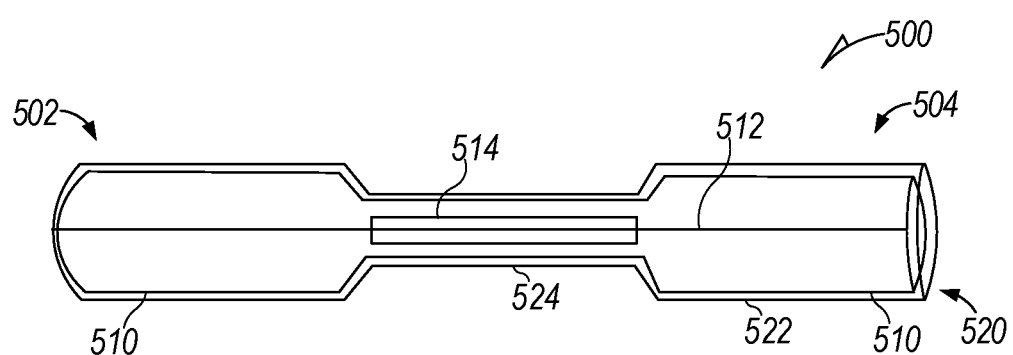
FIG. 5 illustrates a schematic diagram of a device with a sheathed magnetic wire.

FIG. 5 illustrates a schematic diagram of a device 500 with a covered magnetic wire 514, in body lumen 520. The device 500 can include a proximal portion 502, a distal portion 504, a tubular body 505, a sheath 510, magnetizable or magnetic elements 512, and magnetizable or magnetic element cover 514. The tubular body can be in an expanded state and a collapsed state. Device 500 is similar to and contains similar components to device 100, except where otherwise noted.

In device 500, a portion of a magnetizable or magnetic element 512 is sheathed with a cover material 514. The cover material 514 can cover a portion of the magnetizable or magnetic element 512 laterally along the tubular body 505 at a place where magnetization is not desired. The cover material can be magnetically insulating, thin materials that can be adhered to or integrated with a portion of the magnetizable or magnetic element. A cover material can be used where the operator would desire the device 500 to not expand and collapse with a change in magnetic field. For example, such a tailored device could be used in passageways where the diameter or shape of the passageway varies along the lateral length of the passageway. With device 500, body lumen 522 has some portions 522 that maintain patency, and others 514 that do not.

Figure 6:
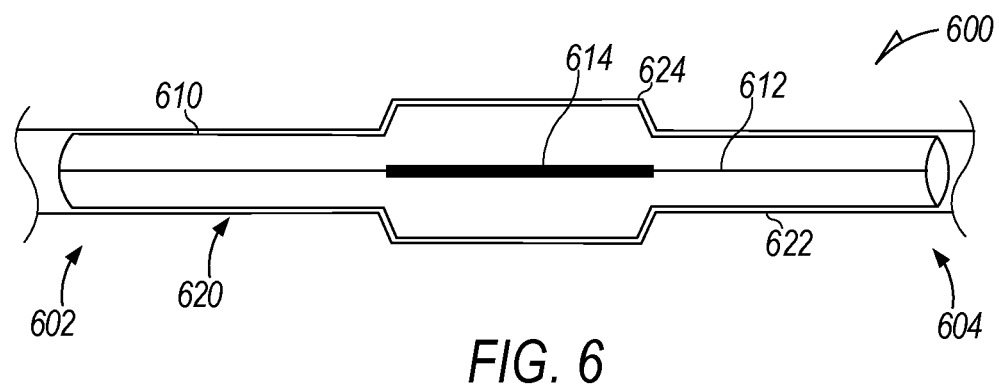
FIG. 6 illustrates a schematic diagram of a device with varying thicknesses of magnetic wire.

FIG. 6 illustrates a schematic diagram of a device 600 with varying thicknesses of magnetic wire 612, 614, in use in body lumen 620. The device 600 can include a proximal portion 602, a distal portion 604, a tubular body 605, a sheath 610, and magnetizable or magnetic elements 612, 614. The tubular body can be in an expanded state and a collapsed state. Device 600 is similar to and contains similar components to device 100, except where otherwise noted.

In device 600, magnetizable or magnetic elements 614 can have a thickness that is greater than that of magnetizable or magnetic elements 614. The thicker magnetizable or magnetic elements 614 can be more responsive to a change in or application of a magnetic field. For example, when actuated so that they repel each other, the magnetizable or magnetic elements 614 may expand the tubular body 605 of the device 600 to a greater diameter than the thinner magnetizable or magnetic elements 612. In this way, the diameter of the device 600 when in an expanded state can vary over the lateral length of the device 600. This can be applied, for example, where the passageway into which the device 600 is used, has a bulbous or wider section at a particular point along the length of the passageway. If the diameter of the expanded state of the device 600 is tailored to match this wider section, patency of the passageway can be maintained despite the bulbous or wider section in the passageway. In use, device 600 can cause the body lumen 620 to maintain patency in a portion 624 near the thicker wire 614, and be more collapsed at portions 622 not near the thickened wire.

Figure 7:
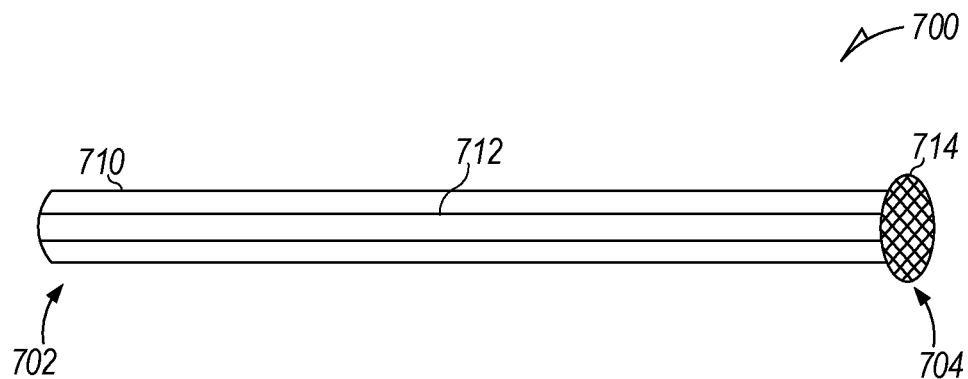
FIG. 7 illustrates a schematic diagram of a device with attached mesh.

FIG. 7 illustrates a schematic diagram of a device 700 with attached mesh. The device 700 can include a proximal portion 702, a distal portion 704, a tubular body 705, a sheath 710, magnetizable or magnetic elements 712, and mesh 714. The tubular body can be in an expanded state and a collapsed state. Device 700 is similar to an contains similar components to device 100, except where otherwise noted.

In device 700, the distal portion 704 can host a mesh 714 on an end of the distal portion 704, extending across the longitudinal lumen of the tubular body 705. The mesh 714 can serve to filter particulates or other debris from entering the tubular body 705, preventing clogging. The mesh can be a metallic, composite, or other bio-compatible material. The mesh can have a size rate of about 0.005" to about 0.02" for blocking of particulates and passage of low viscosity liquids, or a size rate of about 0.010" to about 0.050" for highly viscous liquids. The mesh can be included on the device 700 when the operator intends to place the device 700 in a passageway that may be subject to debris or other particulates that are undesired for passing through the device 700. The mesh can be anchored to or attached to the distal portion 704 of the device 700 through bio compatible adhesive or mechanical fastening mechanisms.

Figure 8:
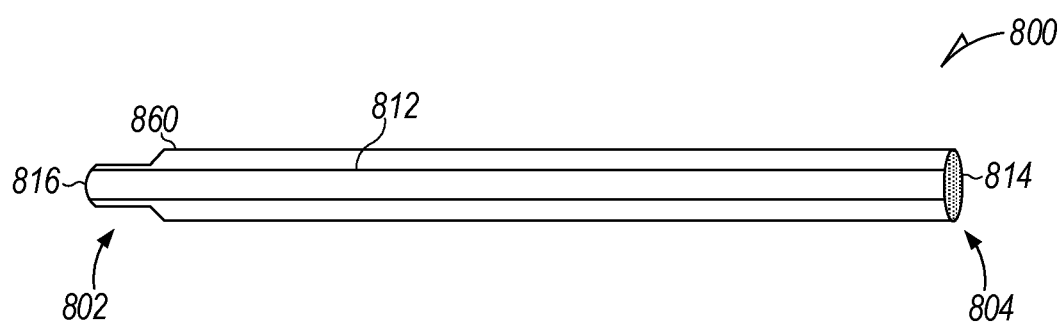
FIG. 8 illustrates a schematic diagram of a device with closed ends.

FIG. 8 illustrates a schematic diagram of a device 800 with closed ends. The device 800 can include a proximal portion 802, a distal portion 804, a tubular body 805, a sheath 810, magnetizable or magnetic elements 812, and ends 814, 816. The tubular body can be in an expanded state and a collapsed state. Device 800 is similar to an contains similar components to device 100, except where otherwise noted.

In device 800, the tubular body 805 can include closed or narrowed ends 814 and 816. Device 800 can be, for example, a plug or other device for preventing flow of fluid and debris through a body passageway, compared to a stent or shunt for the purpose of allowing fluid flow. The ends 814 and 816 can be narrowed or closed with the same material as the sheath 810, such that the ends 814, 816, are collapsible along with the rest of the tubular body 805 when the magnetizable or magnetic elements 812 are actuatable by a change or application of a magnetic field.

Figure 9:
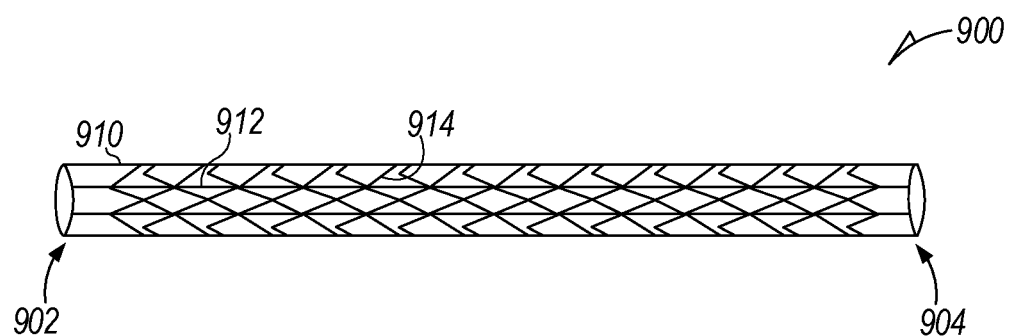
FIG. 9 illustrates a schematic diagram of a stent or shunt with external holding structures.

FIG. 9 illustrates a schematic diagram of a stent or shunt 900 with external holding structures. The device 900 can include a proximal portion 902, a distal portion 904, a tubular body 905, a sheath 910, magnetizable or magnetic elements 912, and external holding structures 914. The tubular body can be in an expanded state and a collapsed state. Device 900 is similar to an contains similar components to device 100, except where otherwise noted.

In device 900, an external surface of the tubular body 905 can include one or more protrusions, features, or shapes, that aid to inhibit migration of the device 900 out of a body passageway that may otherwise naturally move or displace the device 900.

For example, where the device 900 is a urinary stent located in the ureter, which can be an average of about 30 cm in many adults, the ureter will induce movement of urine downward from the kidney to the bladder. The ureter accomplishes this through peristalsis, the radially symmetrical contraction and relaxation of muscles along the ureter wall, that propagates in a wave downwards towards the bladder. In this case, a urinary stent placed in the ureter for an extended period of time may move downwards towards the bladder with peristalsis absent an anchor or other attachment mechanism for the stent.

Unlike conventional stents, the device 900 does not necessarily include pigtail or curled endings to anchor it in the ureter. In contrast, the device 900 can include one or more external holding structures 914 such as a protrusion, anchor, or other shape that can mechanically interact with the wall of the ureter (or other passageway) when the device 900 is in an expanded state, creating a hold even during peristalsis. The external holding structure 914 can mechanically secure the device 900 by pressing against or engaging with a physiological structure, such as the wall of the passageway in which the device 900 is inserted. In some cases, structure 914 can be on the interior of the device 900 to limit the movement of stones, such that stones move in a downward direction. The structure 914 can advantageously limit movement in one direction.

Figure 10:
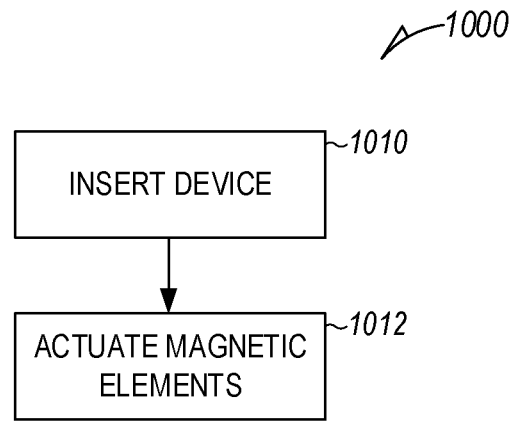
FIG. 10 illustrates a flow chart depicting a method of applying a device such as a stent, shunt, or plug, with magnetically induced expansion.

FIG. 10 illustrates a flow chart depicting a method 1000 of applying a device such as a stent, shunt, or plug, with magnetically induced expansion. Method 1000 can include steps 1010 to 1012 for application of the device.

First, in step 1010, a device such as a stent, shunt, or plug can be inserted, to a desired location, such as into a passageway of a body, by an operator such as a doctor, surgeon, or nurse. When inserted, the device can be in a relatively collapsed state, having a small diameter for easy insertion.

The device can include an elongated tubular body including a proximal portion and a distal portion and defining a collapsible longitudinal lumen of the tubular body therebetween. The tubular body can include a plurality of magnetizable or magnetic elements and a collapsible sheath.

Once inserted, the plurality of magnetizable or magnetic elements can be actuated in step 1012. This can provide magnetic repulsion to encourage the tubular body to maintain a more expanded state, the magnetizable or magnetic elements repelling each other to open the shaft. This can be done through the use of an applicator magnet to apply or change the magnetic field to which the magnetizable or magnetic elements are exposed or the magnetic elements may be pre-magnetized and held in a collapsed state by a outer sheath placed over the tubular body that limits radial expansion due to the repulsive magnetic forces. The actuation may simply involve removal of the outer sheath. This can include actuating the plurality of magnetizable or magnetic elements by drawing a magnetic applicator along or in the elongated tubular body.

Figure 11:
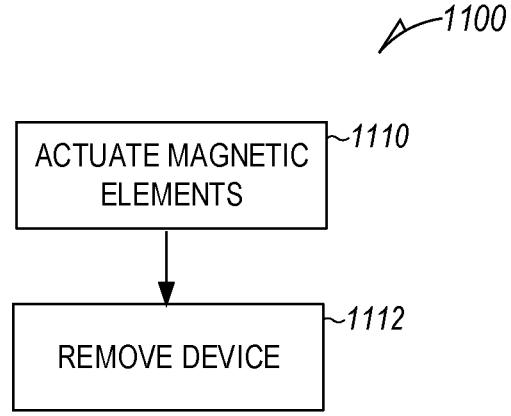
FIG. 11 illustrates a flow chart depicting a method of removal of a device such as a stent, shunt, or plug, with magnetically induced expansion.

FIG. 11 illustrates a flow chart depicting a method of removal of a device such as a stent, shunt, or plug, with magnetically induced expansion. In method 1100, the magnetic elements can be actuated (step 1110) such that the device collapses to a smaller diameter or shape. This can be done, for example, by use of a magnetic actuator, either inserted separately, or part of the device. The actuation can remove or alter the magnetic field in and around the magnetic elements to reduce repulsion therebetween.

Next, the device can be physically removed through the body lumen from the patient (step 1112). This can be done, for example, by mechanical force of withdrawn the collapsed device. The collapsed device can, for example, have a diameter small enough to allow removal with sufficient clearance.

Each of these non-limiting examples can stand on its own, or can be combined in various permutations or combinations with one or more of the other examples.

Example 1 can include a magnetically actuatable dilation device for at least partial insertion into a patient, the device comprising: a deformable elongated tubular body including a proximal portion and a distal portion and defining a longitudinal lumen of the tubular body therebetween, the deformable elongated body capable of an expanded state and a collapsed state, wherein the tubular body includes a sheath and a plurality of magnetizable or magnetic elements for providing magnetic repulsion, after being magnetically actuated, to maintain the tubular body to maintain the expanded state.

Example 2 can include Example 1, wherein the magnetizable or magnetic elements include magnetizable or magnetic elongate members.

Example 3 can include any of Examples 1-2, wherein the magnetizable or magnetic elongate members extend longitudinally along at least a portion of the tubular body.

Example 4 can include any of Examples 1-3, wherein the magnetizable or magnetic elongate members extend laterally along at least a portion of the tubular body.

Example 5 can include any of Examples 1-4, wherein the magnetizable or magnetic elongate members extend spirally around at least a portion of the tubular body.

Example 6 can include any of Examples 1-5, wherein at least one of the magnetizable or magnetic elongate members includes a thickness varying along a length of at least a portion of the at least one of the magnetizable or magnetic elongate members.

Example 7 can include any of Examples 1-6 wherein the magnetizable or magnetic elongate members form braided or interwoven strands along at least a portion of the tubular body.

Example 8 can include any of Examples 1-7, wherein the sheath includes a compliant material extending between ones of the elongate members to define the longitudinal lumen of the tubular body.

Example 9 can include any of Examples 1-8, wherein the longitudinal lumen is closed or narrowed at a location along the tubular body.

Example 10 can include any of Examples 1-9, wherein the longitudinal lumen is closed or narrowed at an end of the tubular body.

Example 11 can include any of Examples 1-10, further comprising a mesh across the longitudinal lumen on or near an end thereof.

Example 12 can include any of Examples 1-11, wherein the tubular body includes at least one lateral protrusion for inhibiting migration of the tubular body, when in a relatively expanded state, by pressing against or engaging a physiological structure.

Example 13 can include any of Examples 1-12, wherein the magnetizable or magnetic elements include dipole elements affixed to the sheath.

Example 14 can include a stent, shunt, or plug device, for at least partial insertion into a patient, the device comprising: a deformable elongated tubular body including a proximal portion and a distal portion and defining a longitudinal lumen of the tubular body therebetween, the deformable elongated body capable of an expanded state and a collapsed state, wherein the tubular body includes a sheath and a plurality of magnetizable or magnetic elements for providing magnetic repulsion, after being magnetically actuated, to maintain the tubular body to maintain the expanded state; and a magnetic applicator.

Example 15 can include Example 14, wherein the magnetic applicator is configured to be drawn through the longitudinal lumen of the tubular body to actuate the plurality of magnetizable or magnetic elements to provide magnetic repulsion to encourage the tubular body to maintain a more expanded state.

Example 16 can include any of Examples 14-15, wherein the magnetic applicator is configured to be drawn through the longitudinal lumen of the tubular body to actuate the plurality of magnetizable or magnetic elements to reduce magnetic repulsion to encourage the tubular body to form a less expanded state.

Example 17 can include any of Examples 14-16, wherein the magnetic applicator includes a coupling to engage the tubular body to permit removal of the tubular body from the patient or relocation of the tubular body within the patient after the tubular body is encouraged to form the less expanded state.

Example 18 can include any of Examples 14-17, wherein the magnetic applicator comprises a ring configured to fit in or around the longitudinal lumen.

Example 19 can include a method of actuating a stent comprising: inserting, to a desired location, a collapsed elongated tubular body including a proximal portion and a distal portion and defining a collapsible longitudinal lumen of the tubular body therebetween, wherein the tubular body includes a plurality of magnetizable or magnetic elements; and actuating the plurality of magnetizable or magnetic elements to provide magnetic repulsion to encourage the tubular body to maintain a more expanded state.

Example 20 can include Example 19, wherein actuating the plurality of magnetizable or magnetic elements comprises drawing a magnetic applicator along the elongated tubular body.

Example 21 can include a method of maintaining patency in a body lumen of a patient comprising: inserting, to a desired location, a collapsed elongated tubular body including a proximal portion and a distal portion and defining a collapsible longitudinal lumen of the tubular body therebetween, wherein the tubular body includes a plurality of magnetizable or magnetic elements; and actuating the plurality of magnetizable or magnetic elements to provide magnetic repulsion such that the tubular body is maintained in an expanded state conforming to walls of the body lumen, thereby maintaining patency in the body lumen.

Example 22 can include Example 21, wherein actuating the plurality of magnetizable or magnetic elements comprises drawing a magnetic applicator along the elongated tubular body.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72 (b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A device for at least partial insertion into a patient, the device comprising:
   a stent comprising a deformable elongated tubular body including a proximal portion and a distal portion and defining a longitudinal lumen of the tubular body therebetween, the tubular body capable of an expanded state and a collapsed state,
   wherein the tubular body includes a sheath and a plurality of magnetizable or magnetic elements for providing magnetic repulsion, after being magnetically actuated, to maintain the tubular body to maintain the expanded state
   wherein the magnetizable or magnetic elements include magnetizable or magnetic elongate members that extend longitudinally along at least a portion of the tubular body,
   wherein the sheath includes a compliant material extending between ones of the magnetizable or magnetic elongate members to define the longitudinal lumen of the tubular body; and
   a magnetic applicator separable from the stent, the magnetic applicator comprising a guide wire and a permanent magnet, the magnetic applicator actuatable for changing the stent between the expanded state and the collapsed state through actuation of the magnetizable or magnetic elements,
   wherein the magnetic applicator is detachable from the stent.

2. The device of claim 1, wherein the magnetic applicator is configured to be drawn through the longitudinal lumen of the tubular body to actuate the plurality of magnetizable or magnetic elements to provide magnetic repulsion to encourage the tubular body to maintain a more expanded state.

3. The device of claim 1, wherein the magnetic applicator is configured to be drawn through the longitudinal lumen of the tubular body to actuate the plurality of magnetizable or magnetic elements to reduce magnetic repulsion to encourage the tubular body to form a less expanded state.

4. The device of claim 3, wherein the magnetic applicator includes an end configured to magnetically engage the magnetic or magnetizable elements of the tubular body to permit removal of the tubular body from the patient or relocation of the tubular body within the patient after the tubular body is encouraged to form the less expanded state.

5. The device of claim 1, wherein the magnetic applicator comprises a ring configured to fit in or around the longitudinal lumen.

6. The device of claim 1, further comprising a mesh extending across the longitudinal lumen at an end of the tubular body.

7. The device of claim 1, wherein the tubular body includes at least one lateral protrusion for inhibiting migration of the tubular body, when in a relatively expanded state, by pressing against or engaging a physiological structure.

8. The device of claim 1, wherein the magnetizable or magnetic elements include dipole elements affixed to the sheath.

* * * * *